United States Patent [19]

Zinke

[11] 4,341,722
[45] Jul. 27, 1982

[54] 2-THIONO-(2H) [1,3,2] DIOXAPHOSPHORINANES (PHOSPHOLANES)

[75] Inventor: Horst Zinke, Ernsthofen, Fed. Rep. of Germany

[73] Assignee: Ciba-Geigy Corporation, Ardsley, N.Y.

[21] Appl. No.: 164,701

[22] Filed: Jun. 30, 1980

[30] Foreign Application Priority Data

Jul. 6, 1979 [CH] Switzerland ........................ 6351/79

[51] Int. Cl.$^3$ .............................................. C07F 9/21
[52] U.S. Cl. .................................. 260/937; 252/46.6; 252/46.7; 260/927 R; 260/970; 260/986
[58] Field of Search ........................... 260/937, 927 R

[56] References Cited

U.S. PATENT DOCUMENTS

| | | | |
|---|---|---|---|
| 2,805,241 | 9/1957 | Sallmann | 260/967 |
| 3,179,688 | 4/1965 | Maier | 260/937 |
| 3,658,953 | 4/1972 | Poel et al. | 260/937 |
| 4,115,559 | 9/1978 | Lacroix et al. | 424/209 |

FOREIGN PATENT DOCUMENTS

| | | | |
|---|---|---|---|
| 410022 | 1/1974 | U.S.S.R. | 260/937 |
| 578315 | 10/1977 | U.S.S.R. | 260/937 |

OTHER PUBLICATIONS

Edmunson, "Chem. Abstracts," vol. 63, (1965), 7013h.

*Primary Examiner*—Anton H. Sutto
*Attorney, Agent, or Firm*—Luther A. R. Hall

[57] ABSTRACT

A process for producing thiophosphorous acid-O,O-diesters from corresponding phosphorous acid diester chlorides and hydrogen sulfide, in which process the acid acceptor used is ammonia. The thiophosphorous acid diesters obtained are suitable as intermediates for producing lubricant additives, fungicides or pharmaceutical products.

2 Claims, No Drawings

2-THIONO-(2H) [1,3,2] DIOXAPHOSPHORINANES (PHOSPHOLANES)

The present invention relates to a novel process for producing thiophosphorous acid diesters, to novel thiophosphorous acid diesters, and to their use as intermediates.

The manner of producing thiophosphorous acid diesters from phosphorous acid diester chloride and hydrogen sulfide is known for example from the U.S. Pat. No. 2,805,241, wherein the acid acceptors used are tert. nitrogen bases, such as dimethylanilide, triethylamine or pyridine. The commercial carrying out of this process is however costly since the use of relatively expensive tert. amines necessitates the filtration of the amine hydrochlorides and the subsequent recovery of the employed amines.

The subject matter of the present invention is a process for producing thiophosphorous acid diesters on a large commercial scale, in a simple manner and also in a yield higher than that hitherto obtained. The invention relates to a process for producing thiophosphorous acid diesters of the formula

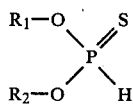

(I)

wherein $R_1$ and $R_2$ independently of one another are each $C_1$–$C_{18}$-alkyl, $C_5$–$C_{12}$-cycloalkyl, phenyl or $C_7$–$C_9$-aralkyl each of which is unsubstituted or is substituted by one or two $C_1$–$C_{12}$-alkyl groups, or $R_1$ and $R_2$ are each $C_2$–$C_{10}$-alkoxyalkyl or $C_3$–$C_{20}$-alkoxycarbonylalkyl, or $R_1$ and $R_2$ together are a bivalent radical of the formula II

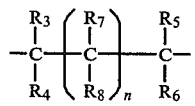

(II)

wherein n is nought or 1, and $R_3$, $R_4$, $R_5$ and $R_6$ independently of one another are each hydrogen, $C_1$–$C_4$-alkyl, cyclohexyl or phenyl, and $R_3$, when n is nought, is also —$CH_2Z$, in which Z is —$XR_{10}$, —$N(R_{11})R_{12}$, —S—P(-S)—(OR$_{10}$)$_2$ or a group of the formula III

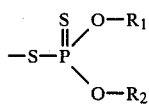

(III)

wherein $R_1$ and $R_2$ have the given meanings, X is oxygen or sulfur, and $R_{10}$, $R_{11}$ and $R_{12}$ independently of one another are each $C_1$–$C_{18}$-alkyl, $C_5$–$C_{12}$-cycloalkyl, phenyl or $C_7$–$C_9$-aralkyl each of which is unsubstituted or is substituted by one or two $C_1$–$C_{12}$-alkyl groups, or $R_{10}$, $R_{11}$ and $R_{12}$ are each $C_2$–$C_{10}$-alkoxyalkyl or $C_3$–$C_{20}$-alkoxycarbonylalkyl, and $R_7$ and $R_8$ independently of one another are each hydrogen, $C_1$–$C_4$-alkyl, cyclohexyl, phenyl, nitro, cyano, $C_2$–$C_{19}$-alkoxycarbonyl, $C_2$–$C_{18}$-alkanoyl, or a group of the formula ($R_9$—O)$_2$—P(O)—, in which $R_9$ is $C_1$–$C_{18}$-alkyl, or $R_7$ and $R_8$ together are 2-butenylene or 2-pentenylene, which process comprises reacting a compound of the formula

(IV)

wherein $R_1$ and $R_2$ have the meanings given above, with hydrogen sulfide in the presence of ammonia.

The ammonia in this process surprisingly acts as an acid acceptor, and does not react in the expected manner with the P-Cl starting material of the formula IV.

Preferably, ammonia gas and hydrogen sulfide gas are introduced at a temperature of $-10°$ to $+40°$ C., particularly $+5°$ to $+20°$ C., into a solution of a compound of the formula IV in an inert organic solvent. The flow of gas can be so finely regulated that the $H_2S$ and $NH_3$ consumption corresponds approximately to the stoichiometric amounts. An excess of $H_2S$ is however possible. All solvents which are inert to the reactants are suitable, for example: aliphatic hydrocarbons, such as ligroin, special gasoline or petroleum ether; cycloaliphatic hydrocarbons, such as cyclohexane; aromatic hydrocarbons, such as benzene, toluene or xylene; chlorinated hydrocarbons, such as methylene chloride or chlorobenzene; ethers, such as diethyl ether, dioxane or tetrahydrofuran; and also dimethylamide and dimethylsulfoxide. Solvents preferably used are nonpolar solvents having a boiling point in the range of 40°–150° C.

The pressure at which the process according to the invention is performed is not critical; preferably however it is not greatly different from normal pressure.

In the formula I, the substituents $R_1$ and $R_2$ can have identical or different meanings. Compounds in which $R_1$ and $R_2$ are identical are preferred.

As $C_1$–$C_{18}$-alkyl, $R_1$, $R_2$, $R_9$, $R_{10}$, $R_{11}$ and $R_{12}$ are for example methyl, ethyl, n-propyl, isopropyl, n-butyl, sec-butyl, tert-butyl, n-hexyl, 2-ethylhexyl, 6-methylheptyl, n-octyl, straight-chain or branched-chain nonyl, decyl, dodecyl, tridecyl, tetradecyl or octadecyl. Preferred alkyl groups have 3–13 C atoms.

As $C_5$–$C_{12}$-cycloalkyl and particularly as $C_6$–$C_{10}$-cycloalkyl, $R_1$, $R_2$, $R_{10}$, $R_{11}$ and $R_{12}$ can be for example: cyclopentyl, cyclohexyl, cyclooctyl, cyclodecyl or cyclododecyl. Cyclohexyl is preferred.

If $R_1$, $R_2$, $R_{10}$, $R_{11}$ and $R_{12}$ are phenyl or $C_7$–$C_9$-aralkyl, these aromatic radicals can be substituted by one or two alkyl groups having 1–12 C atoms, preferably 1–9 C atoms. Examples of alkyl substituents of this kind are methyl, ethyl, isopropyl, n-butyl, sec-butyl, tert-butyl, tert-amyl, n-hexyl, n-octyl, 1,1,3,3-tetramethylbutyl or 1,1,3,3,5,5-hexamethylhexyl. When $R_1$, $R_2$, $R_{10}$, $R_{11}$ and $R_{12}$ are $C_7$–$C_9$-aralkyl, it can be α,α-dimethylbenzyl, preferably β-phenylethyl and particularly benzyl.

Where $R_1$, $R_2$, $R_{10}$, $R_{11}$ and $R_{12}$ are $C_2$–$C_{10}$-alkoxyalkyl, the alkyl moiety can contain 1–3 C atoms, and the alkoxy moiety 1–8 C atoms, for example in methoxymethyl, ethoxymethyl, 2-methoxyethyl, 2-ethoxyethyl, 2-n-butoxyethyl, 3-n-butoxyethyl, 2-octoxyethyl or methoxypropyl. To be mentioned in particular are compounds in which $R_1$, $R_2$, $R_{10}$, $R_{11}$ and $R_{12}$ as alkoxyalkyl contain 3–6 C atoms.

As $C_3$–$C_{20}$-alkoxycarbonylalkyl wherein the alkyl moiety contains 1–3 C atoms and the alkoxycarbonyl moiety 2–18 C atoms, $R_1$, $R_2$, $R_{10}$, $R_{11}$ and $R_{12}$ are for example: methoxycarbonylmethyl, propoxycarbonylmethyl, butoxycarbonylmethyl, octoxycarbonylmethyl, dodecoxycarbonylmethyl, octadecoxycarbonylmethyl, methoxycarbonylethyl, ethoxycarbonylethyl, octadecoxycarbonylethyl or methoxycarbonylpropyl. Preferably, $R_1$, $R_2$, $R_{10}$, $R_{11}$ and $R_{12}$ contain as alkoxycarbonylalkyl 4–10 C atoms.

If $R_3$, $R_4$, $R_5$, $R_6$, $R_7$ and $R_8$ are $C_1$–$C_4$-alkyl, they are for example: methyl, ethyl, n-propyl, isopropyl, n-butyl, sec-butyl or tert-butyl.

$R_7$ and $R_8$ as $C_2$–$C_{19}$-alkoxycarbonyl are for example: methoxycarbonyl, ethoxycarbonyl, butoxycarbonyl, hexoxycarbonyl, octoxycarbonyl, dodecoxycarbonyl or octadecoxycarbonyl. Preferred alkoxycarbonyl groups contain 2–9 C atoms.

$R_7$ and $R_8$ as $C_2$–$C_{18}$-alkanoyl can be for example: formyl, acetyl, butyryl, hexanoyl, octanoyl, dodecanoyl or octadecanoyl. $C_2$–$C_8$-alkanoyl groups are preferred.

n is nought or 1. Compounds of the formula I to be emphasised are those wherein n is 1.

When $R_3$ is a group of the formula III, only one such group may be contained in the molecule.

The process is suitable especially for compounds of the formula I wherein $R_1$ and $R_2$ independently of one another are each $C_3$–$C_{13}$-alkyl, $C_6$–$C_{10}$-cycloalkyl, phenyl or $C_7$–$C_8$-aralkyl each of which is unsubstituted or is substituted by one or two $C_1$–$C_4$-alkyl groups, or $R_1$ and $R_2$ are each $C_3$–$C_6$-alkoxyalkyl or $C_4$–$C_{10}$-alkoxycarbonylalkyl, or $R_1$ and $R_2$ together form a radical of the formula II in which $R_3$, $R_4$, $R_5$ and $R_6$ independently of one another are each hydrogen or $C_1$–$C_4$-alkyl, and $R_7$ and $R_8$ independently of one another are each hydrogen, $C_1$–$C_4$-alkyl, cyclohexyl, phenyl, nitro, $C_2$–$C_9$-alkoxycarbonyl or $C_2$–$C_8$-alkanoyl, or $R_7$ and $R_8$ together are 2-butenylene or 2-pentenylene, and n is nought or 1; and for those compounds wherein $R_3$, if n is nought, is additionally —$CH_2$—Z, in which Z is —$XR_{10}$, —$N(R_{11})R_{12}$, —S—$P(S)(OR_{10})_2$ or a group of the formula III, and $R_{10}$, $R_{11}$ and $R_{12}$ independently of one another are each $C_{1-18}$-alkyl, $C_{5-12}$-cycloalkyl, phenyl or $C_7$–$C_9$-aralkyl each of which is unsubstituted or is substituted by one or two $C_1$–$C_{12}$-alkyl groups, or $R_{10}$, $R_{11}$ and $R_{12}$ are each $C_2$–$C_{10}$-alkoxyalkyl or $C_3$–$C_{20}$-alkoxycarbonylalkyl.

The compounds of the formula IV can be produced, in a known manner (cp. Houben-Weyl "Methoden der organischen Chemie", Vol. 12/2, pp. 45–51), from the alcohols $R_1$-OH and $R_2$-OH, wherein $R_1$ and $R_2$ have the meanings defined in the foregoing, and phosphorus trichloride.

As far as novel compounds are concerned, subject matter of the present invention embraces also compounds of the formula IV wherein $R_1$ and $R_2$ form a bivalent radical of the formula II, $R_3$, $R_4$, $R_5$ and $R_6$ have the meanings already defined, n is nought or 1, and $R_3$, if n is nought, is —$CH_2$—Z in which Z is —S—$R_{10}$, —$N(R_{11})R_{12}$, —S—$P(S)(OR_{10})_2$ or a radical of the formula III, $R_{10}$, $R_{11}$ and $R_{12}$ have the meanings given in the foregoing, and $R_7$ and $R_8$ independently of one another are each CN, $C_2$–$C_{19}$-alkoxycarbonyl, $C_2$–$C_{18}$-alkanoyl, or a group of the formula $(R_9O)_2P(O)$—, $R_9$ has the meaning given above, $R_7$ has the meaning given above and $R_7$ is also hydrogen, $C_1$–$C_4$-alkyl, cycloalkyl or phenyl.

The compounds of the formula I wherein $R_1$ and $R_2$ are a group of the formula II in which n is nought or 1, and $R_3$, $R_4$, $R_5$ and $R_6$ are, if n is 1, independently of one another each hydrogen, $C_1$–$C_4$-alkyl, cyclohexyl or phenyl, and $R_3$, if n is nought, is also —$CH_2$—Z, in which Z is —$XR_{10}$, —$N(R_{11})R_{12}$, —S—$P(S)$—$(OR_{10})_2$, or a group of the formula III, whereby X, $R_{10}$, $R_{11}$ and $R_{12}$ have the meanings given above, and $R_7$ and $R_8$ independently of one another are each $NO_2$, CN, $C_2$–$C_{19}$-alkoxycarbonyl, $C_2$–$C_{18}$-alkanoyl, or a group $(R_9$—$O)_2$—$P(O)$—, wherein $R_9$ has the meaning given above, or $R_7$ and $R_8$ together are 2-butenylene or 2-pentenylene, and $R_7$ is also hydrogen, $C_1$–$C_4$-alkyl, cyclohexyl or phenyl, are novel compounds and therefore also form subject matter of the present invention. With regard to their respective definitions, the symbols $R_3$ to $R_{12}$ can correspond to any one of the meanings given above as examples.

Compounds to be emphasised among the novel compounds are especially those corresponding to the formula I wherein $R_1$ and $R_2$ form a group of the formula II, n is 1, and $R_3$, $R_4$, $R_5$ and $R_6$ have the meanings given above, and $R_7$ and $R_8$ independently of one another are $C_2$–$C_{19}$-alkoxycarbonylalkyl, $C_2$–$C_{18}$-alkanoyl, $NO_2$ or $(R_9O)_2P(O)$—, and $R_7$ is also hydrogen or $C_1$–$C_4$-alkyl; and also those compounds wherein $R_5$, if n is nought, is —$CH_2$—Z, in which Z is —$XR_{10}$, —$N(R_{11})R_{12}$, —S—$P(S)(OR_{10})_2$, or a radical of the formula III, where $R_9$, X, $R_{10}$, $R_{11}$ and $R_{12}$ have the meanings given above.

The novel compounds of the formula I can of course be produced by known methods, for instance by reacting the appropriate chlorides of the formula IV with hydrogen sulfide in the presence of a tertiary amine, such as pyridine or triethylamine. They are however produced more advantageously by the "ammonia process" described above.

The novel compounds are valuable starting materials for producing lubricant-additives, fungicides and pharmaceutical substances; they are furthermore themselves suitable as additives in mineral and synthetic lubricants since they protect the devices to be lubricated against frictional wear and have no corrosive action on the parts to be protected.

Even in very small amounts, the novel compounds of the formula I are effective as anti-wear additives in lubricants. Thus, mineral and synthetic lubricating oil, as well as mixtures thereof, which contain 0.001 to 5 percent by weight, preferably 0.02 to 3 percent by weight, relative to the lubricant, of a compound of the formula I have excellent high-pressure lubricating properties, which are clearly manifested in the greatly reduced wear phenomena on the parts to be lubricated. The lubricants concerned are commonly known to one skilled in the art, and are described for example in the "Schmiermittel Taschenbuch" ("Lubricants Handbook") [Hüthig Verlag, Heidelberg, 1974].

The lubricating oil formulation can additionally contain other additives which are added in order to improve certain basic oil properties, for example additives such as antioxidants, metal passivators, rust inhibitors, agents for improving the viscosity index, pour-point depressors, dispersants/detergents, and other additives which protect against wear.

Examples of antioxidants are:

(a) alkylated and non-alkylated aromatic amines and mixtures thereof, for example: dioctyldiphenylamine, mono-t-octylphenyl-α- and -β-naphthylamines, phenothiazine, dioctylphenothiazine, phenyl-α-naphthylamine and N,N'-di-sec-butyl-p-phenylenediamine;

(b) sterically hindered phenols, for example: 2,6-di-tert-butyl-p-cresol, 4,4'-bis-(2,6-diisopropylphenol), 2,4,6-triisopropylphenol, 2,2'-thio-bis-(4-methyl-6-tert-butylphenol) and 4,4'-methylene-bis-(2,6-di-tert-butylphenol);

(c) alkyl phosphites, aryl phosphites or alkaryl phosphites, for example: trinonyl phosphite, triphenyl phosphite and diphenyldecyl phosphite;

(d) esters of thiodipropionic acid or thiodiacetic acid, for example: dilauryl thiodipropionate or dioctyl thiodiacetate;

(e) salts of carbamic and dithiophosphoric acids, for example: antimony diamyldithiocarbamate and zinc diamyldithiophosphate; and (f) combinations of two or more antioxidants from the above, for example: an alkylated amine and a sterically hindered phenol.

Examples of metal passivators are:

(a) for copper, for example: benzotriazole, tetrahydrobenzotriazole, 2-mercaptobenzothiazole, 2,5-dimercaptothiadiazole, salicylidene-propylenediamine and salts of salicylaminoguanidine;

(b) for lead, for example: sebacic acid derivatives, quinizarine and propyl gallate; and (c) a combination of two or more of the above additives.

Examples of rust inhibitors are:

(a) organic acids and their esters, metal salts and anhydrides, for example: N-oleoyl-sarcosine, sorbitane monooleate, lead naphthenate and dodecenylsuccinic anhydride;

(b) nitrogen-containing compounds, for example:

I. primary, secondary or tertiary aliphatic or cycloaliphatic amines and amine salts of organic and inorganic acids, for example oil-soluble alkyl-ammonium carboxylates, and II. heterocyclic compounds, for example: substituted imidazolines and oxazolines;

(c) phosphorus-containing compounds, for example: amine salts of phosphoric acid partial esters;

(d) sulfur-containing compounds, for example: barium dinonylnaphthalene-sulfonates and calcium petroleum sulfonates; and (e) combinations of two or more of the above additives.

Examples of agents which improve the viscosity index are for example: polymethacrylates, vinylpyrrolidone/methacrylate copolymers, polybutenes, olefine copolymers and styrene/acrylate copolymers.

Examples of pour-point depressors are for example: polymethacrylates and alkylated naphthalene derivatives.

Examples of dispersants/detergents are for example: polybutenylsuccinic acid imides, polybutenylphosphonic acid derivatives and hyperbasic sulfonates and phenolates of magnesium, calcium and barium.

Examples of other additives which provide protection against wear are for example: compounds which contain sulfur and/or phosphorus and/or halogen, such as vegetable oils treated with sulfur, zinc dialkyldithiophosphates, tritolyl phosphate, chlorinated paraffins, alkyl disulfides and aryl disulfides.

The Examples which follow illustrate the invention.

EXAMPLE 1

2-Chloro-5-methyl-5-butoxycarbonyl-1,3,2-dioxaphosphorinane 68.70 g (0.50 mol) of phosphorus trichloride in 50 ml of toluene were added dropwise with vigorous stirring, in the course of 1 hour, to a solution of 95.15 g (0.50 mol) of 2,2-bis-hydroxymethylpropionic acid butyl ester in 250 ml of toluene at 5°–10° C. The reaction mixture was subsequently stirred for 1 hour without cooling in a water-jet vacuum, during which time a gentle flow of $N_2$ was fed in; the solvent was then distilled off in vacuo (bath temperature = 50° C./15–20 mm Hg), and the residue was purified by vacuum distillation. The product obtained was in the form of a colourless liquid; $n_D^{20} = 1.4701$; b.p. 113°–115° C./0.1 mm Hg.

Analysis: calculated: 42.4% C, 6.4% H 12.2% P 13.9% Cl. found: 43.0% C 6.3% H 12.2% P 13.4% Cl.

EXAMPLES 2 AND 3

The compounds 2 and 3 shown below were synthetised according to Example 1.

| Example | Compound | b.p. (°C./mm Hg) | $N_D^{20}$ | % P cal. found |
|---|---|---|---|---|
| 2 | 2-chloro-5,5-diethoxy-carbonyl-1,3,2-dioxaphosphorinane | 124–127° C. /0.2 | 1.4681 | 10.9 11.0 |
| 3 | 4-chloro-3,5,4-dioxy-phosphorinanespiro-(3-cyclohexene) | 102–103° C. /0.4 | 1.5254 | 15.0 15.2 |

EXAMPLE 4

2-Chloro-4-[(diisooctyloxythiophosphoryl)-thiomethyl]-1,3,2-dioxaphospholane 14.82 g (0.20 mol) of freshly distilled 2,3-epoxypropanol were added with stirring, in the course of half an hour, to a solution of 70.92 g (0.20 mol) of dithiophosphoric acid-O,O-di-2-ethylhexyl ester in 100 ml of toluene, and the mixture was subsequently stirred for half an hour at 65°–70° C. Without intermediate isolation, the addition product obtained was cyclised, according to Example 1, with 27.46 g (0.20 mol) of phosphorus trichloride to give phosphorus acid diester chloride. The solvent was then distilled off in vacuo (bath temperature 50° C./15–20 mm Hg), and the residue freed in an oil-pump vacuum from solvent residues.

Yield: 95.6 g (97% of theory) of a light-yellow liquid; $n_D^{20} = 1.5014$.

EXAMPLE 5

2-Chloro-4-[isooctyloxy-carbonyl-methyl)-thiomethyl]-1,3,2-dioxaphospholane

A solution of 41.76 g (0.15 mol) of S-2,3-dihydroxypropylthioglycolic acid isooctyl ester in 100 ml of toluene was added dropwise at −10° C. in the course of 1 hour, with vigorous stirring, to a solution of 20.6 g (0.15 mol) of phosphorus trichloride and 31.87 g (0.315 mol) of triethylamine in 100 mol of toluene. The reaction mixture was subsequently stirred for half an hour at −10° C. and for 3 hours at room temperature, and the triethylamine hydrochloride which had precipitated was filtered off. The solvent was distilled off in vacuo (bath temperature 30° C./1–2 mm Hg) and the residue freed in an oil-pump vacuum from solvent residues.

Yield: 44.7 g (87% of theory) of a light-yellow liquid; $n_D^{20} = 1.4996$.

EXAMPLE 6

2-Thiono-(2H)-5,5-dimethyl[1,3,2]dioxaphosphorinane

Into a solution of 168.6 g (1.0 mol) of 2-chloro-5,5-dimethyl-1,3,2-dioxaphosphorinane in 700 ml of toluene at a temperature of ≦10° C. was fed, for about 2½ hours with vigorous stirring, a uniform stream of hydrogen sulfide and ammonia in such a manner that no noticeable losses of gas occurred. Stirring was subsequently maintained for 3 hours at room temperature and, after the flow of gas had been turned off, rinsing was performed for half an hour with nitrogen. The reaction mixture was then washed four times with 500 ml of water each time, dried with sodium sulfate, and the solvent was distilled off in vacuo. The crystalline residue obtained was thoroughly stirred up with 300 ml of petroleum ether, filtered off, washed with petroleum ether and dried in vacuo at 50° C. until a constant weight was attained.

Yield: 145.4 g (87% of theory) of colourless crystals, melting point 83.5°-86° C., acid number 0.18 mg of KOH/g.

EXAMPLES 7-14

The Examples listed in Table 2 were synthesised according to Example 1 and purified by distillation.

TABLE 2

| Ex. No. | Compound | m.p. (°C.) | b.p. (°C./mm Hg) | $N_{20}^D$ | Yield (% of theory) | % P cal. found |
|---|---|---|---|---|---|---|
| 7 | 2-thiono-(2H)-5-ethyl-5-butyl-1,3,2-dioxaphosphorinane | — | 111-128°/0,2 | 1,5075 | 89 | 13,9 13,9 |
| 8 | 4-thiono-(4H)-3,5,4-dioxaphosphorinane-spiro-(3-cyclohexene) | 118-121° (1) | — | — | 92 | 15,2 15,1 |
| 9 | 2-thiono-(2H)-5-methyl-5-butoxycarbonyl-1,3,2-dioxaphosphorinane | — | 170°/0,1 (2) | 1,4940 | 73 | 12,3 12,3 |
| 10 | 2-thiono-(2H)-5,5-diethoxycarbonyl-1,3,2-dioxaphosphorinane | 66,5-67,5° | — | — | 96 | 11,0 11,0 |
| 11 | 2-thiono-(2H)-4,5-dimethyl-1,3,2-dioxaphospholane | — | 84°/4 | 1,4996 | 95 | 20,4 20,1 |
| 12 | 2-thiono-(2H)-5-methyl-5-phenyl-1,3,2-dioxa-phosphorinane | 77-79 | — | — | 85 | 13,6 13,6 |
| 13 | 2-thiono-(2H)-5-methyl-5-propyl-1,3,2-dioxaphosphorinane | 29-32 | 124°/0.13 | — | 88 | 15,9 16,0 |
| 14 | 2-thiono-(2H)-5-methyl-5-nitro-1,3,2-dioxaphosphorinane | 112-114 (3) | — | — | 96 | 15,7 15,9 |

(1) after recrystallisation from toluene
(2) molecular distillation with decomposition
(3) after digestion with butylacetate

EXAMPLE 15

2-Thiono-(2H)-5,5-dimethyl-1,3,2-dioxaphosphorinane Synthesis with pyridine as acid acceptor Into a solution, cooled to 5° C., of 84.3 g (0.5 mol) of 2-chloro-5,5-dimethyl-1,3,2-dioxaphosphorinane and 43.5 g (0.55 mol) of pyridine in 500 ml of toluene was fed hydrogen sulfide, with cooling, until no further noticeable absorption of gas could be observed. The pyridine hydrochloride which had precipitated was filtered off, and washed with toluene, and the solvent was then distilled off in vacuo from the filtrate and washing liquid. The resulting crystalline residue was recrystallised from cyclohexane/i-propanol (2:1).

Yield: 64.1 g (77% of theory) of colourless crystals, melting point 80°-84.5° C., acid number 0.28 mg of KOH/g.

A comparison of the yield using this process with the yield obtained with the process according to the invention described in Example 6 demonstrates the superiority of the "ammonia process".

EXAMPLE 16 tert-Dodecyl-/tetradecylammonium-2,2-thiono-thiol-5,5-dimethyl-1,3,2-dioxaphosphorinane A mixture of 83.1 g (0.50 mol) of 2-thiono-(2H)-5,5-dimethyl-1,3,2-dioxaphosphorinane, 16.0 g (0.50 mol) of sulfur and 97.3 g (0.50 mol) of a primary tert-dodecyl-/tetradecylamine mixture (neutral equivalent 194.7) was slowly stirred, in the courses of which the temperature rose to 70°-80° C. and a clear liquid was formed. Stirring was continued for 1 hour at 80° C. and for 3 hours at 120°-130° C.

Yield: 196 g (99% of theory) of a light-yellow highly-viscous liquid.

| Analysis: | % C | % H | % N | % P | % S |
|---|---|---|---|---|---|
| calculated: | 54.1 | 10.1 | 3.6 | 7.9 | 16.3 |
| found: | 53.9 | 10.0 | 3.6 | 7.9 | 16.2 |

This Example demonstrates the use of a compound of the formula I according to the invention as an intermediate. The compound according to Example 16 is suitable as an additive in lubricating oils.

EXAMPLE 17 tert-Dodecyl-/tetradecylammonium-2,2-thiono-thiol-4-
S-(diisooctyloxythiophosphoryl)-thiomethyl-1,3,2-
dioxaphospholane 14.82 g (0.20 mol) of freshly distilled 2,3-epoxypropanol was added with stirring, in the course of half an hour, to a solution of 70.92 g (0.20 mol) of dithiophosphoric acid-O,O-di-2-ethylhexyl ester in 100 ml of toluene, and the mixture was subsequently stirred at 65°–70° C. for half an hour. Without intermediate isolation, the addition product obtained was firstly cyclised according to Example 1 with 27.46 g (0.20 mol) of phosphorus trichloride to give phosphorus acid diester chloride, and this was further reacted according to Example 6 with hydrogen sulfide/ammonia to the corresponding 2-thiono-(2H)-[1,3,2]-dioxaphospholane. To the toluene solution of the product obtained were subsequently added, with stirring, 6.41 g (0.20 mol) of sulfur and 40.3 g (0.20 mol) of a primary tert-dodecyl-/tetradecylamine mixture (neutral equivalent 201.5), and the whole was stirred at 50° C. for 2 hours. After cooling of the reaction mixture, it was washed with water and 5% sodium sulfate solution and dried with sodium sulfate, and the solvent was distilled off in vacuo.

Yield: 134.1 g (93% of theory) of a viscous, light-yellow liquid; $n_D^{20}=1.5162$; acid number: calculated 77.5, found 76.9.

| Analysis: | % N | % P |
|---|---|---|
| calculated: | 1.9 | 8.6 |
| found: | 2.0 | 8.6. |

EXAMPLE 18

Thiophosphorous acid-O,O-diethyl ester

Hydrogen sulfide and ammonia were fed in a uniform stream at room temperature, with vigorous stirring, into a solution of 263 g (1.68 mol) of phosphorous acid diethyl ester chloride (production according to German Offenlegungsschrift No. 2,643,442 from triethyl phosphite and phosphorus trichloride) in 1000 ml of petroleum benzine (40/60). The reaction mixture warmed up to 40° C. and was held at this temperature by water cooling. After completion of the reaction, flushing was carried out with nitrogen for ¾ of an hour with stirring. The ammonium chloride which precipitated was filtered off, and the solvent was distilled off from the filtrate under reduced pressure. The residue was purified by vacuum distillation.

Yield: 219 g (85% of theory) of colourless liquid, b.p. 77°–82° C./18–19 mm Hg.

What is claimed is:

1. A compound of formula I

wherein $R_1$ and $R_2$ together form a group of formula II

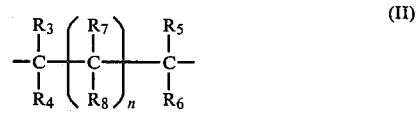

in which n is nought or 1, when n is 1, $R_3$, $R_4$, $R_5$ and $R_6$ independently of one another are each hydrogen, $C_1$–$C_4$-alkyl, cyclohexyl or phenyl, and when n is nought, $R_4$, $R_5$ and $R_6$ are as defined above, $R_3$ is —$CH_2Z$ in which Z is —$XR_{10}$, —$N(R_{11})R_{12}$, —S—$P(S)(OR_{10})_2$ or a group of formula III

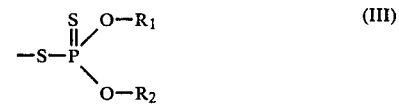

wherein $R_1$ and $R_2$ are as defined above, X is oxygen or sulfur, $R_{10}$, $R_{11}$ and $R_{12}$ independently of one another are each $C_1$–$C_{18}$ alkyl, $C_5$–$C_{12}$-cycloalkyl, phenyl, $C_7$–$C_9$-aralkyl, or said phenyl or said $C_7$–$C_9$-aralkyl substituted by one or two $C_1$–$C_{12}$-alkyl groups, or $R_{10}$, $R_{11}$ and $R_{12}$ are each $C_2$–$C_{10}$-alkoxyalkyl or $C_3$–$C_{20}$-alkoxycarbonylalkyl, and $R_7$ and $R_8$ independently of one another are each nitro, cyano, $C_2$–$C_{19}$-alkoxycarbonyl, $C_2$–$C_{18}$-alkanoyl or a group $(R_9O)_2P(O)$— in which $R_9$ is $C_1$–$C_{18}$-alkyl, or $R_7$ and $R_8$ together are 2-butenylene or 2-pentenylene, or $R_7$ can also be hydrogen, $C_1$–$C_4$-alkyl, cyclohexyl or phenyl.

2. A compound according the claim 1 wherein n is 1, $R_7$ and $R_8$ independently of one another are each $C_2$–$C_{19}$-alkoxycarbonylalkyl, or together are 2-pentenylene, or $R_7$ can also be hydrogen or $C_1$–$C_4$-alkyl.

* * * * *